(12) United States Patent
Crohn

(10) Patent No.: US 7,153,131 B2
(45) Date of Patent: Dec. 26, 2006

(54) INTRAORAL ILLUMINATION DEVICE

(75) Inventor: Bobby Crohn, Highland Mills, NY (US)

(73) Assignee: Crohn Enterprises Ltd., Highland Mills, NY (US)

( * ) Notice: Subject to any disclaimer, the term of this patent is extended or adjusted under 35 U.S.C. 154(b) by 39 days.

(21) Appl. No.: 11/051,080

(22) Filed: Feb. 7, 2005

(65) Prior Publication Data

US 2006/0177793 A1    Aug. 10, 2006

(51) Int. Cl.
    A61C 1/00       (2006.01)
    F21K 2/00       (2006.01)

(52) U.S. Cl. .......................................... 433/29; 362/34

(58) Field of Classification Search ................. 433/29; 362/34
    See application file for complete search history.

(56) References Cited

U.S. PATENT DOCUMENTS

| | | | |
|---|---|---|---|
| 1,122,086 A * | 12/1914 | Dunlop ........................ | 600/238 |
| 1,266,659 A | 5/1918 | Brannan | |
| 1,380,344 A | 7/1921 | Bassett | |
| 1,533,605 A | 4/1925 | Pelton et al. | |
| 3,576,987 A | 5/1971 | Voight et al. | |
| 3,700,879 A | 10/1972 | Franc | |
| 3,894,225 A | 7/1975 | Chao | |
| 4,405,973 A | 9/1983 | Moscarillo | |
| 4,589,846 A | 5/1986 | Annoni | |
| 5,007,924 A | 4/1991 | Jekel | |
| 5,179,938 A | 1/1993 | Lonky | |
| 5,277,173 A | 1/1994 | Cantele | |
| 5,329,938 A | 7/1994 | Lonky | |
| 5,566,679 A * | 10/1996 | Herriott ........................ | 600/551 |
| 5,692,895 A | 12/1997 | Farzin-Nia et al. | |
| 5,718,577 A * | 2/1998 | Oxman et al. .................. | 433/37 |
| 6,183,249 B1 * | 2/2001 | Brennan et al. ................ | 433/9 |
| 6,235,148 B1 * | 5/2001 | Courson et al. .......... | 156/379.6 |
| 6,299,441 B1 | 10/2001 | Novak | |
| 6,332,776 B1 | 12/2001 | Martin et al. | |
| 6,496,718 B1 | 12/2002 | Lonky | |
| 6,499,995 B1 * | 12/2002 | Schwartz ........................ | 433/6 |
| 6,616,447 B1 * | 9/2003 | Rizoiu et al. .................. | 433/29 |
| 2002/0026124 A1 * | 2/2002 | Whitaker ...................... | 600/551 |
| 2003/0097122 A1 * | 5/2003 | Ganz et al. ..................... | 606/7 |
| 2004/0010299 A1 * | 1/2004 | Tolkoff et al. ................. | 607/88 |
| 2004/0018241 A1 | 1/2004 | House et al. | |
| 2004/0043349 A1 | 3/2004 | Liao | |
| 2004/0063060 A1 | 4/2004 | Meyers et al. | |
| 2005/0080465 A1 * | 4/2005 | Zelickson et al. ............. | 607/88 |
| 2005/0237730 A1 * | 10/2005 | Barnes ......................... | 362/34 |
| 2005/0254227 A1 * | 11/2005 | Bilodeau ...................... | 362/34 |

* cited by examiner

Primary Examiner—Ralph A. Lewis
(74) Attorney, Agent, or Firm—Michael E. Zall

(57) ABSTRACT

An intraoral illumination device for illuminating the interior of the mouth of a dental patient. The device comprises a flexible container having container defining walls, a portion of the walls being light transmitting. The device is sized for insertion into the mouth and placement against an interior surface of the mouth, e.g., the gum. A pressure-sensitive adhesive layer covers a portion of the walls for adhesively mounting the device to the interior surface of the mouth. A first chamber and a second chamber are within the container. The chambers are connected to each other by a frangible wall. Each of the chambers contain a chemical composition that when mixed together create a chemiluminescent reaction that produces light. When the frangible wall is fractured by flexing the container, it permits the compositions to mix within the container to create a chemiluminescent reaction that emits light through the container walls to illuminate the mouth, permitting dental procedures to be easily performed.

7 Claims, 3 Drawing Sheets

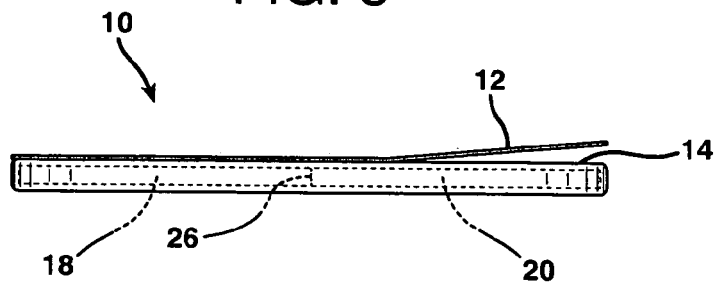
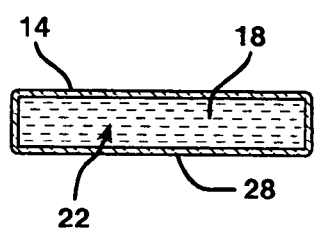
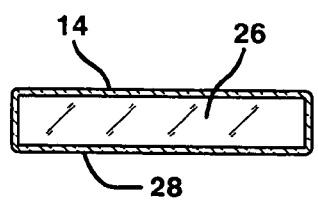
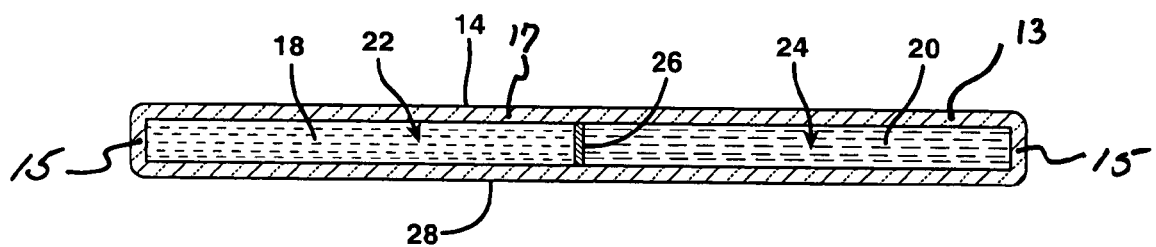

INTRAORAL ILLUMINATION DEVICE

BACKGROUND OF THE INVENTION

1. Field of the Invention

This invention relates to the field of devices for illuminating the interior of the mouth to permit dental procedures to be easily performed.

2. Description of the Related Art

The broad concept of lighting the interior of the mouth for dental purposes is well known. In widespread use in the dental profession are overhead lights which the practitioner must continually attempt to position in such a way that he or she does not come between the light and the patient, blocking the light from its intended target. Various devices have incorporated a light source in attempts to overcome this problem. Devices that have been used include lights which are hand held, those mounted on portable moving instruments, and overhead lights which attempt to beam or reflect light into the tooth.

Some examples of existing prior art include the following:

US Pub. No. 2004/0063060 to Meyers et al describes an intraoral illumination device that includes a pair of light units held in place by a flexible band placed between the gums and lips of the user. The light source is placed over the molars in the back of the mouth. The light source can be an ultraviolet light. An adhesive may be used to affix the device to the roof of the mouth. The lights are preferably powered by battery and can be activated by the user. The invention also contemplates a chemiluminescent light. Various means, other than the flexible band, are described to secure the device in the mouth without the band.

U.S. Pat. No. 6,332,776 to Martin et al. describes a lighted dental prop comprising a wedge-shaped bite block and a light source. The bite block utilizes reflected fiberoptic light or an internal light source to provide broad illumination to the mouth.

U.S. Pat. No. 1,122,086 to Dunlop describes a device that includes adjustable means for propping the jaws apart and a means for illuminating the mouth.

U.S. Pat. No. 4,589,846 to Annoni describes a tooth transilluminating light holder that secures a lighting device to a tooth so that both surfaces of the tooth can be viewed. High intensity light is conducted along fiberoptic lines and can be adjusted to obtain proper proximity of the light to the tooth's surface.

U.S. Pat. No. 6,299,441 to Novak describes a novelty mouthpiece that contains removable chemiluminescent inserts and when the holder is flexed it breaks the barrier and mixes the chemiluminescent solution and activator to produce chemiluminescent light inside the mouth of a user.

US Pub. No. 2004/0043349 to Liao describes an illuminated device, such as a mouth guard, pacifier or a set of false teeth, that is either held within or by a user's mouth. The device includes at least one light source, a battery for providing power to the light source and an on/off switch for selectively activating the light source.

U.S. Pat. No. 5,692,895 to Farzin-Nia et al describes orthodontic appliances coated with a luminescent pigment.

U.S. Pat. No. 1,266,659 to Brannan describes a small clamp equipped with an incandescent lamp that can be clamped to a tooth to provide light in the mouth.

U.S. Pat. No. 5,277,173 to Cantele describes a disposable laryngoscope that has a container that provides chemiluminescent light.

U.S. Pat. No. 3,576,987 to Ridgefield et al., describes a chemiluminescent light means that is a self-contained light unit comprising an outer flexible, cylindrical, light transmitting container for one reactive composition, and an inner, rigid container for another reactive composition. Flexing the outer container breaks the inner container, allowing the reactive compositions to mix and produce a reaction providing chemiluminescent light which is visible through the outer light transmitting container.

US Publication No. 2004/0018241 to Houze et al. describes a bioadhesive composition in a flexible, finite form for the topical application to skin or mucous membranes of an active ingredient, such as an analgesic.

There is also a product sold under the brand name DentiPatch® by Noven Pharmaceuticals, Inc. (Miami, Fla.). It is believed that this product is described in the above patent to Houze et al. The product is a small flexible unit that when adhered to the buccal mucosa provides topical anesthesia by releasing lidocaine.

U.S. Pat. No. 5,007,924 to Jekel describes a baby pacifier having a removable clip-on luminescent sheath/handle.

U.S. Pat. No. 4,405,973 to Moscarillo describes an emergency chemiluminescent light source which can be mounted on an object by an adhesive ring on the base of the light.

U.S. Pat. No. 3,894,225 to Chao describes a tape of mini-lamps.

Other U.S. patents of interest include: U.S. Pat. No. 3,700,879 to Franc; U.S. Pat. No. 1,533,605 to Pelton et al.; U.S. Pat. No. 1,509,041 to Hyams; and U.S. Pat. No. 1,380,344 to Bassett.

As shown in much of the prior art, dental devices which incorporate a light source are generally complicated, multi-element devices, each of which must each be manufactured separately, and then assembled by hand. The labor required is likely to result in a retail price which makes it unlikely that such devices will be discarded after use with one patient. Further, the design of many such devices requires a size which fills a significant portion of the mouth, and therefore leaves less maneuvering room available to the dental practitioner.

The invention described and claimed herein is directed to an easy to use, inexpensive, disposable, intraoral illuminating device for the mouth that allows the practitioner to easily perform the tasks that need to be performed without interference from the illuminating device.

OBJECTS AND SUMMARY OF INVENTION

It is an object of this invention to provide an inexpensively-manufactured, low-cost intraoral illuminating device.

It is yet another object of this invention to provide an intraoral illuminating device that can be easily positioned and secured in the mouth.

It is also an object of the invention to provide an intraoral illuminating device that does not take up the limited space in the mouth, permitting the dental practitioner to easily maneuver the dental instruments therein and perform the required procedures.

It is a further object of the invention to provide an intraoral illuminating device that is sufficiently low in cost so that it is disposable.

All of the foregoing objects as well as others are achieved by the intraoral illuminating device of this invention that is used for illuminating the interior of the mouth of a dental patient. The device comprises a flexible container having container defining walls, a portion of the walls being light transmitting. The device is sized for insertion into the mouth and placement against an interior surface of the mouth, e.g., the gum. A pressure-sensitive adhesive layer covers a portion of the walls so that the device can be adhesively mounted to the interior surface of the mouth. Preferably, the adhesive layer is covered by a layer of release paper to protect it prior to use.

A first chamber and a second chamber are provided within the container. The chambers are connected to each other by a frangible wall. The first chamber contains a first chemical composition and the second chamber contains a second chemical composition. When the first and second chemical compositions are mixed together a chemiluminescent reaction takes place that produces light. When the frangible wall is fractured by flexing the container, it permits the first and second chemicals to mix within the container to create a chemiluminescent reaction that emits light through the portion of the container walls that are light transmitting to thereby illuminate the mouth and permit easy viewing of the interior of the mouth and for dental procedures to be easily performed therein without interference from the illuminating device.

In use, the container is flexed to fracture the frangible wall, the release paper removed and the device adhered to the interior of the mouth to thereby light it and permit a clear view of the interior.

BRIEF DESCRIPTION OF THE DRAWINGS

For a more complete understanding of the present invention, reference may be had to the following description of the exemplary preferred embodiments of the present invention considered in connection with the accompanying drawings, of which:

FIG. 3 is side view of the intraoral illuminating device shown in FIG. 1 showing the release paper being removed to expose the pressure-sensitive adhesive;

FIG. 4 is a cross-sectional view taken along 4—4 of FIG. 2 through the width of one of the chambers within the intraoral illuminating device of this invention;

FIG. 5 is a cross-sectional view taken along 5—5 of FIG. 2 through the width and through the frangible wall between the chambers;

FIG. 6 is a cross-sectional view taken along 6—6 of FIG. 2 through the length of the intraoral illuminating device of this invention.

DETAILED DESCRIPTION OF THE INVENTION

Figure 1:
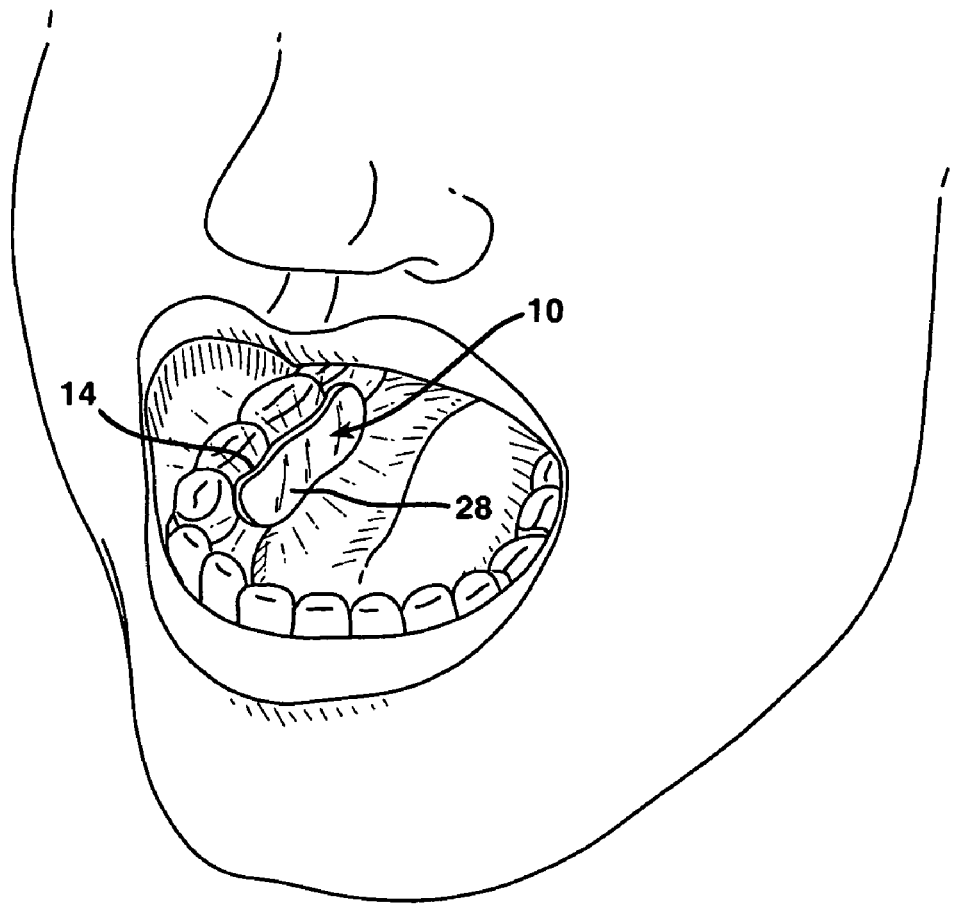
FIG. 1 is a perspective view of one embodiment of the intraoral illuminating device in use in a dental patient's mouth.

Referring to FIGS. 1–7, the intraoral illumination device 10 is used for illuminating the interior of the mouth of a dental patient. The device 10 comprises a flexible container, generally having container defining walls 13. In the embodiment depicted, the container walls comprise a top wall 17, a bottom wall 28 and sidewalls 15 connecting the top and bottom walls 17, 28. A portion of the walls 13 are light transmitting. For maximum light transmission and ease of manufacture of the device, it is preferred that the walls 17, 15 and 28 are all light transmitting.

It is preferred that appropriate polymers (plastics) be used for the walls 17, 15 and 28 both for ease of manufacture, cost and properties. The container is preferably made of a flexible transparent or translucent material, having sufficient rigidity to maintain its shape and sufficient flexibility to be fractured and shaped to conform to the surface, e.g., gum line, with which it comes into contact and is capable of maintaining the contact so as to facilitate adherence of the device 10 thereto. Preferably the container is formed from a transparent or translucent food-grade polymer material. Such materials include, but are not limited to polyethylene, polypropylene, PTFE (Teflon®, Dupont, Inc.) and the like having the appropriate flexibility and rigidity.

The device 10 is dimensioned so that it can be inserted in the mouth and adhered to a small area of soft tissue therein and not interfere with any dental procedures to be performed. The container is of a size that permits the easy insertion of the device into the mouth and placement against an interior surface of the mouth, e.g., gum. Preferably the device 10 is an elongated strip or cylinder similar to that depicted in FIGS. 1–7. The length, for example, may range from about 0.25 inches to about 1 inch, but longer and shorter lengths may be used. The width or diameter may range from 0.05 inches to 0.5 inches, with less and greater widths contemplated by this invention. Some of the factors that enter into determining the length and width of the device are the intensity of chemiluminescence activity, the strength of the adhesive as well as the size of the mouth.

Figure 2:
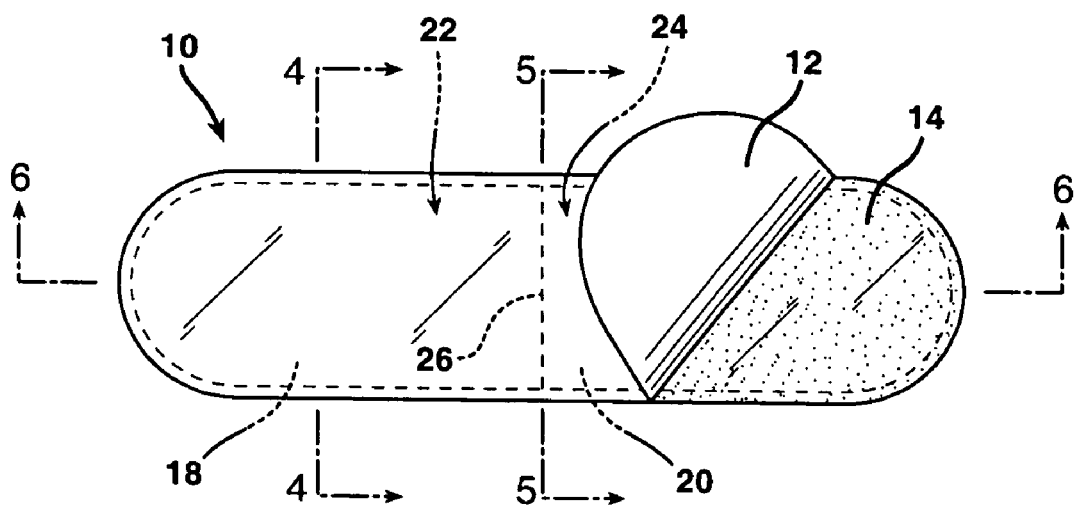
FIG. 2 is a plan view of the intraoral illuminating device shown in FIG. 1 showing the release paper being removed to expose pressure-sensitive adhesive.

A pressure-sensitive adhesive layer 14 is provided that covers a portion of the container walls 17. The adhesive layer 14 is used for adhesively mounting the container to the interior surface of the mouth. The adhesive can be the bio-adhesives described in U.S. Publication No. 2004/0018241 to Houze, but this invention contemplates the use of any adhesive suitable for effective and safe adherence of the device 10 to soft tissues or teeth. Referring to FIGS. 2 and 3, preferably the pressure-sensitive adhesive layer 14 is covered by a layer of release paper 12 which may be provided with a pull tab. The release paper 12 serves to keep the pressure-sensitive adhesive 14 free of any accumulation of foreign matter until the intraoral illumination device is put to use. Just prior to use the paper 12 is removed to reveal the pressure-sensitive adhesive layer 14.

Referring to FIGS. 3–7, within the container is a first chamber 18 and a second chamber 20. The chambers 18, 20 are connected to each other by a frangible wall 26. The frangible wall 26 is a rigid, breakable, i.e., frangible, material such as glass, or a relatively brittle thermoset resin, e.g., thin walled Bakelite, or other suitable material and need not be transparent or translucent.

The first chamber 18 contains a first chemical composition 22 and the second chamber 20 contains a second chemical composition 24. The first and second chemical compositions 22, 24 are selected so that when mixed together a chemiluminescent reaction takes place that produces light. Preferably, the first chamber 18 contains a chemiluminescent solution 22 and the second chamber 20 contains an activator 24 for the chemiluminescent solution.

Typically, the first composition 22 is an oxalate solution containing a fluorescent dye, and the second composition 24 is an activator solution. In order to provide chemiluminescence, the activator 24 and the oxalate solution 22 must be mixed. However, the chemiluminescence will eventually fade. In the preferred embodiment the chemicals 22, 24 are selected to provide light for a sufficient length of time to permit complection of the dental procedure. However, if not completed the expended intraoral illuminating device 10 can be easily removed from the mouth and another device activated and adhered to the same location or one that is close to the original location.

There are numerous chemiluminescent systems that are known and can be used with the intraoral illuminating device of this invention. Broadly, the intraoral illuminating device of this invention must accommodate the admixture of at least two chemiluminescent components. Broadly, the components comprise either (a) a component containing a chemiluminescent compound and a second component containing a hydroperoxide compound, either or both components containing a diluent, or (b) a dry solid component containing both a solid chemiluminescent compound and a solid hydroperoxide compound and a second component comprising a solvent for said solid chemiluminescent compound and said solid hydroperoxide compound. This invention contemplates the addition of other necessary ingredients to the components for the control of, for example, longevity of the light, intensity of the light, shelf-life, etc. In particular with the oxalic-type chemiluminescent compounds of this invention, a fluorescent compound must be included in the system.

Additionally, the wavelength of the light emitted by chemiluminescence, i.e., the color of the light emitted, may be varied by the addition of any one or more energy transfer agents (fluorescers) such as the known fluorescent compounds. The wavelength of the light emitted by the composition of this invention will vary, depending upon the particular fluorescent component employed in the reaction.

There are many benefits to the use of chemiluminescent light. Chemiluminescent light is preferred because no source of electricity is required. Since the device 10 requires no externally generated source of energy, the intraoral device can be made small, highly portable and disposable. Moreover, chemiluminescent light is a relatively cold light that will not heat the areas of the gums that the device is attached to. Chemiluminescent light is also effective under wet environments like, the mouth, making it safe because there are no electrical connections to short out.

The device 10 of the invention may also be used to produce ultraviolet rays. In such an embodiment, the chemicals that are mixed are designed to generate ultraviolet light. The illuminating devices 10 can then be placed at any desired location in the mouth to enable localized high-intensity curing of traditional dental adhesives.

Figure 7:
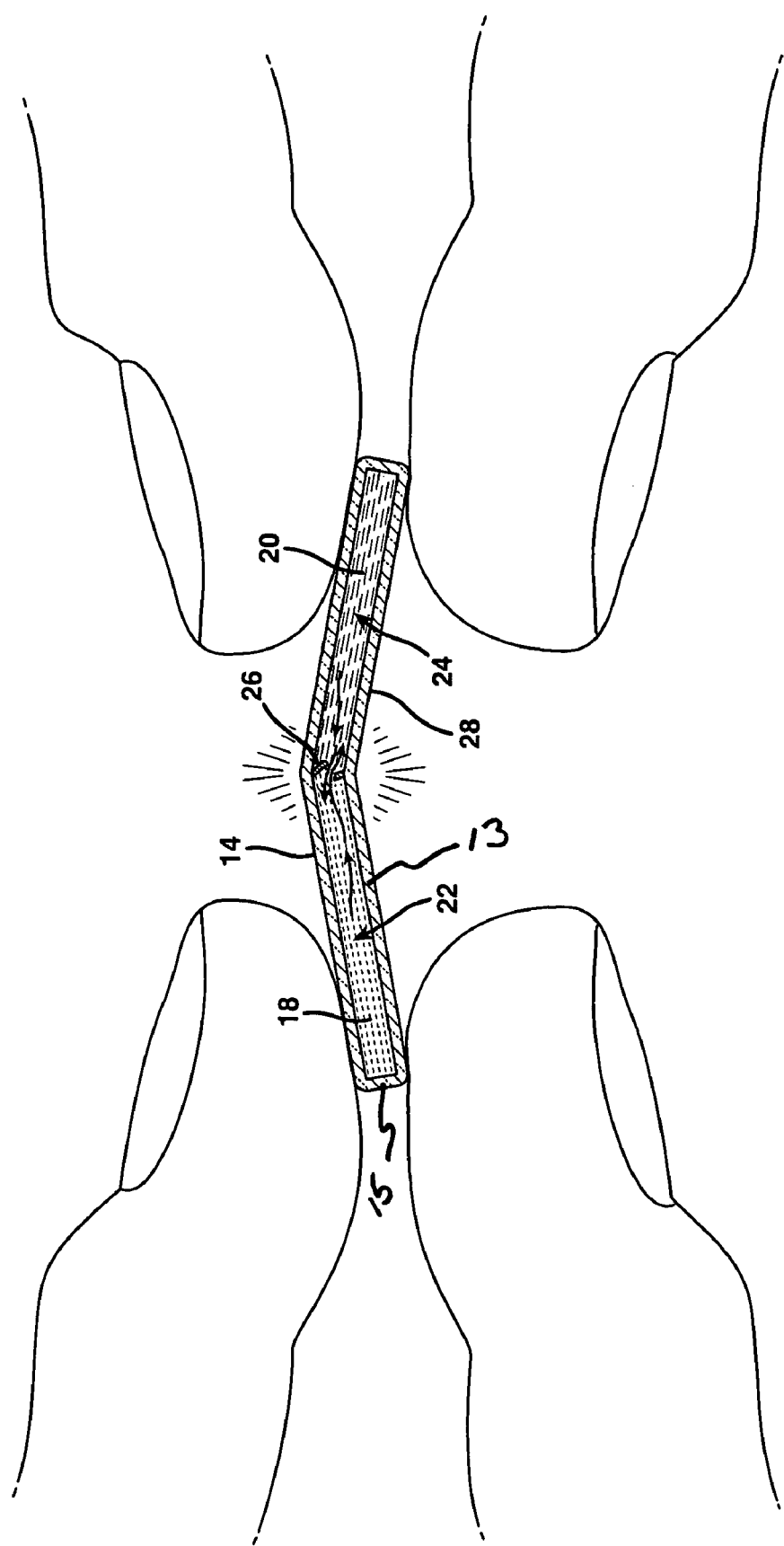
FIG. 7 is a schematic view of the intraoral illuminating device being flexed to fracture the frangible wall to activate the chemiluminescence process prior to use in a patient's mouth.

Referring to FIG. 7, in use, the frangible wall 26 is fractured by flexing the container. This permits the first and second chemicals 22, 24 to mix within the container to create a chemiluminescent reaction that emits light through the portion of the container walls. Referring to FIGS. 2 and 3, subsequently the release paper 12 is removed and the device 10 is then pressed, shaped and adhered to the soft tissue at the gum line and/or teeth as depicted in FIG. 1. The light emitted illuminates the mouth and permits the dental procedures to be performed therein.

Another structure for the chemiluminescent light means that may be used in the device of this invention is disclosed, for example, in U.S. Pat. No. 3,576,987 to Ridgefield et al., the entire disclosure of which is incorporated herein by reference. The device is a self-contained light unit comprising an outer flexible, cylindrical, light transmitting container for one reactive composition, and an inner, rigid container for another reactive composition. Flexing the outer container breaks the inner container, allowing the reactive compositions to mix and produce a reaction providing chemiluminescent light which is visible through the outer light transmitting container.

Due to the wide range of possibilities for the chemiluminescent light source, the invention has a wide range of uses. For example, when the light source is used to generate traditional white light, a dentist can put the device 10 inside the mouth of a user simply to enhance the visible field. However, when the light source generates light in the ultraviolet spectrum, the device 10 may be used to cure dental materials.

This device is small and unobtrusive so that it does not get in the way of the practitioner and the assistant as they access the mouth with various dental instruments. The device is also designed with few components and with ease of manufacture as a criterion, to provide for very low manufacturing costs. The intent is that the lighted dental prop will be sufficiently affordable that every dental practitioner will discard it after use with a single patient, and preventing any possibility of cross contamination between patients as may exist with other known devices.

The foregoing constitutes a description of specific embodiments showing how the invention may be applied and put into use. These embodiments are only exemplary. The invention in its broadest, and more specific aspects, is further described and defined in the claims which now follow.

These claims, and the language used therein, are to be understood in terms of the variants of the invention which have been described. They are not to be restricted to such variants, but are to be read as covering the full scope of the invention as is implicit within the invention and the disclosure.

What is claimed is:

1. An intraoral illumination device for illuminating interior surfaces of the mouth of a dental patient, the device comprising:
    a flexible container having container defining walls, a first portion of the walls of the container being light transmitting to permit the transmission of light therethrough, the container of a size that permits insertion of the device into the mouth and placement against a mounting portion of the interior surfaces of the mouth;
    a pressure-sensitive adhesive layer covering a second portion of the walls of the container for adhesively mounting the second portion of the walls to the mounting portion of the interior surfaces of the mouth and preventing the transmission of light to the mounting portion of the interior surfaces of the mouth;
    the second portion of the container defining walls permitting the transmission of light therethrough to the remaining portions of the interior surfaces of the mouth;
    a first chamber and a second chamber within the container, the chambers connected to each other by a frangible wall;
    wherein the first chamber contains a first chemical composition and the second chamber contains a second chemical composition, wherein when the first and second chemical compositions are mixed together a chemiluminescent reaction takes place that produces light;
    whereby the frangible wall is fractured by flexing the container, permitting the first and second chemicals to mix within the container to create a chemiluminescent reaction that emits light through the first portion of the container walls that are light transmitting to thereby illuminate the remaining interior surfaces of the mouth and permit dental procedures to be performed therein.

2. The intraoral illumination device of claim 1, wherein the container is a unitary flexible molded unit.

3. The intracral illumination device of claim 1, wherein the container is substantially elongated and cylindrical and the first chamber is on one end of the container and the second chamber on the other end of the container with the frangible wall between the chambers.

4. The intraoral illumination device of claim 1, wherein the pressure-sensitive adhesive layer has a removable protective release paper adhered to the layer.

5. The intraoral illumination device of claim 1, wherein the container walls are translucent or transparent.

6. The intraoral illumination device of claim 1, wherein the adhesive is a bio-adhesive.

7. The intraoral illumination device of claim 1, wherein the light produced is ultraviolet.

* * * * *